United States Patent
Jafari et al.

(10) Patent No.: US 9,302,061 B2
(45) Date of Patent: Apr. 5, 2016

(54) EVENT-BASED DELAY DETECTION AND CONTROL OF NETWORKED SYSTEMS IN MEDICAL VENTILATION

(75) Inventors: Mehdi M. Jafari, Laguna Hills, CA (US); Edward R. McCoy, Vista, CA (US); Rhomere S. Jimenez, San Diego, CA (US); Gail F. Upham, Fallbrook, CA (US)

(73) Assignee: Covidien LP, Mansfield, MA (US)

( * ) Notice: Subject to any disclaimer, the term of this patent is extended or adjusted under 35 U.S.C. 154(b) by 1313 days.

(21) Appl. No.: 12/714,135

(22) Filed: Feb. 26, 2010

(65) Prior Publication Data
US 2011/0209704 A1    Sep. 1, 2011

(51) Int. Cl.
*A61M 16/00* (2006.01)
*A61M 16/08* (2006.01)

(52) U.S. Cl.
CPC ....... *A61M 16/0051* (2013.01); *A61M 16/0833* (2014.02); *A61M 2016/0021* (2013.01); *A61M 2016/0036* (2013.01); *A61M 2205/35* (2013.01); *A61M 2205/3507* (2013.01); *A61M 2205/3561* (2013.01); *A61M 2205/3569* (2013.01); *A61M 2205/505* (2013.01); *A61M 2230/005* (2013.01)

(58) Field of Classification Search
CPC ................... A61M 16/0051; A61M 2230/005; A61M 2205/3507
See application file for complete search history.

(56) References Cited

U.S. PATENT DOCUMENTS

| | | |
|---|---|---|
| 3,267,933 A | 8/1966 | Mills et al. |
| 3,868,567 A | 2/1975 | Ekstrom et al. |
| 4,752,089 A | 6/1988 | Carter |
| 4,921,642 A | 5/1990 | LaTorraca |
| 4,954,799 A | 9/1990 | Kumar |
| 5,057,822 A | 10/1991 | Hoffman |
| 5,072,737 A | 12/1991 | Goulding |

(Continued)

FOREIGN PATENT DOCUMENTS

WO    WO 2009/146312 A1    12/2009

OTHER PUBLICATIONS

Cummings et al., "Role of an endoplasmic reticulum Ca2+-independent phospholipase A2 in oxidant-induced renal cell death", Am. J. Physiol. Renal Physiol 283: F492-F498 (2002).*

(Continued)

*Primary Examiner* — Nathan R Price
*Assistant Examiner* — Anh Bui
(74) *Attorney, Agent, or Firm* — Merchant & Gould P.C.

(57) ABSTRACT

This disclosure describes systems and methods for detecting and quantifying transmission delays associated with distributed sensing and monitoring functions within a ventilatory system. Specifically, the present methods and systems described herein define an event-based delay detection algorithm for determining transmission delays between distributed signal measurement and processing subsystems and a central platform that receives data from these subsystems. It is important to evaluate and quantify transmission delays because dyssynchrony in data communication may result in the misalignment of visualization and monitoring systems or instability in closed-loop control systems. Generally, embodiments described herein seek to quantify transmission delays by selecting a ventilator-based defining event as a temporal baseline and calculating the delay between the inception of the defining event and the receipt of data regarding the defining event from one or more distributed sensing devices.

12 Claims, 4 Drawing Sheets

(56) References Cited

U.S. PATENT DOCUMENTS

| | | | |
|---|---|---|---|
| 5,150,291 A | 9/1992 | Cummings et al. | |
| 5,161,525 A | 11/1992 | Kimm et al. | |
| 5,237,987 A | 8/1993 | Anderson et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |
| 5,319,540 A | 6/1994 | Isaza et al. | |
| 5,325,861 A | 7/1994 | Goulding | |
| 5,333,606 A | 8/1994 | Schneider et al. | |
| 5,339,807 A | 8/1994 | Carter | |
| 5,343,857 A | 9/1994 | Schneider et al. | |
| 5,351,522 A | 10/1994 | Lura | |
| 5,356,787 A * | 10/1994 | Gross | 435/18 |
| 5,357,946 A | 10/1994 | Kee et al. | |
| 5,368,019 A | 11/1994 | LaTorraca | |
| 5,383,449 A | 1/1995 | Forare et al. | |
| 5,385,142 A | 1/1995 | Brady et al. | |
| 5,390,666 A | 2/1995 | Kimm et al. | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,438,980 A | 8/1995 | Phillips | |
| 5,443,075 A | 8/1995 | Holscher | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,221 A | 7/1996 | Power | |
| 5,542,415 A | 8/1996 | Brady | |
| 5,544,674 A | 8/1996 | Kelly | |
| 5,549,106 A | 8/1996 | Gruenke et al. | |
| 5,570,346 A | 10/1996 | Shur | |
| 5,596,984 A | 1/1997 | O'Mahoney et al. | |
| 5,630,411 A | 5/1997 | Holscher | |
| 5,632,270 A | 5/1997 | O'Mahoney et al. | |
| 5,645,048 A | 7/1997 | Brodsky et al. | |
| 5,660,171 A | 8/1997 | Kimm et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,715,812 A | 2/1998 | Deighan et al. | |
| 5,762,480 A | 6/1998 | Adahan | |
| 5,771,884 A | 6/1998 | Yarnall et al. | |
| 5,791,339 A | 8/1998 | Winter | |
| 5,794,986 A | 8/1998 | Gansel et al. | |
| 5,813,399 A | 9/1998 | Isaza et al. | |
| 5,826,575 A | 10/1998 | Lall | |
| 5,829,441 A | 11/1998 | Kidd et al. | |
| 5,864,938 A | 2/1999 | Gansel et al. | |
| 5,865,168 A | 2/1999 | Isaza | |
| 5,881,717 A | 3/1999 | Isaza | |
| 5,881,723 A | 3/1999 | Wallace et al. | |
| 5,884,623 A | 3/1999 | Winter | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,934,274 A | 8/1999 | Merrick et al. | |
| 6,024,089 A | 2/2000 | Wallace et al. | |
| 6,041,780 A | 3/2000 | Richard et al. | |
| 6,047,860 A | 4/2000 | Sanders | |
| 6,076,523 A | 6/2000 | Jones et al. | |
| 6,116,240 A | 9/2000 | Merrick et al. | |
| 6,116,464 A | 9/2000 | Sanders | |
| 6,123,073 A | 9/2000 | Schlawin et al. | |
| 6,135,106 A | 10/2000 | Dirks et al. | |
| 6,142,150 A | 11/2000 | O'Mahoney | |
| 6,161,539 A | 12/2000 | Winter | |
| 6,220,245 B1 | 4/2001 | Takabayashi et al. | |
| 6,269,812 B1 | 8/2001 | Wallace et al. | |
| 6,273,444 B1 | 8/2001 | Power | |
| 6,283,119 B1 | 9/2001 | Bourdon | |
| 6,305,373 B1 | 10/2001 | Wallace et al. | |
| 6,321,748 B1 | 11/2001 | O'Mahoney | |
| 6,325,785 B1 | 12/2001 | Babkes et al. | |
| 6,357,438 B1 | 3/2002 | Hansen | |
| 6,360,745 B1 | 3/2002 | Wallace et al. | |
| 6,369,838 B1 | 4/2002 | Wallace et al. | |
| 6,412,483 B1 | 7/2002 | Jones et al. | |
| 6,439,229 B1 | 8/2002 | Du et al. | |
| 6,467,478 B1 | 10/2002 | Merrick et al. | |
| 6,546,930 B1 | 4/2003 | Emerson et al. | |
| 6,553,991 B1 | 4/2003 | Isaza | |
| 6,557,553 B1 | 5/2003 | Borrello | |
| 6,571,795 B2 | 6/2003 | Bourdon | |
| 6,622,726 B1 | 9/2003 | Du | |
| 6,644,310 B1 | 11/2003 | Delache et al. | |
| 6,668,824 B1 | 12/2003 | Isaza et al. | |
| 6,675,801 B2 | 1/2004 | Wallace et al. | |
| 6,718,974 B1 | 4/2004 | Moberg | |
| 6,725,447 B1 | 4/2004 | Gilman et al. | |
| 6,739,337 B2 | 5/2004 | Isaza | |
| 6,761,167 B1 | 7/2004 | Nadjafizadeh et al. | |
| 6,761,168 B1 | 7/2004 | Nadjafizadeh et al. | |
| 6,814,074 B1 | 11/2004 | Nadjafizadeh et al. | |
| 6,866,040 B1 | 3/2005 | Bourdon | |
| 6,960,854 B2 | 11/2005 | Nadjafizadeh et al. | |
| 7,036,504 B2 | 5/2006 | Wallace et al. | |
| 7,077,131 B2 | 7/2006 | Hansen | |
| RE39,225 E | 8/2006 | Isaza et al. | |
| 7,117,438 B2 | 10/2006 | Wallace et al. | |
| 7,270,126 B2 | 9/2007 | Wallace et al. | |
| 7,369,757 B2 | 5/2008 | Farbarik | |
| 7,370,650 B2 | 5/2008 | Nadjafizadeh et al. | |
| 7,428,902 B2 | 9/2008 | Du et al. | |
| 7,460,959 B2 | 12/2008 | Jafari | |
| 7,487,773 B2 | 2/2009 | Li | |
| 7,654,802 B2 | 2/2010 | Crawford, Jr. et al. | |
| 7,694,677 B2 | 4/2010 | Tang | |
| 7,717,113 B2 | 5/2010 | Andrieux | |
| D618,356 S | 6/2010 | Ross | |
| 7,784,461 B2 | 8/2010 | Figueiredo et al. | |
| 7,823,588 B2 | 11/2010 | Hansen | |
| 7,855,716 B2 | 12/2010 | McCreary et al. | |
| D632,796 S | 2/2011 | Ross et al. | |
| D632,797 S | 2/2011 | Ross et al. | |
| 7,891,354 B2 | 2/2011 | Farbarik | |
| 7,893,560 B2 | 2/2011 | Carter | |
| D638,852 S | 5/2011 | Skidmore et al. | |
| 7,984,714 B2 | 7/2011 | Hausmann et al. | |
| D643,535 S | 8/2011 | Ross et al. | |
| 7,992,557 B2 | 8/2011 | Nadjafizadeh et al. | |
| 8,001,967 B2 | 8/2011 | Wallace et al. | |
| 8,021,310 B2 | 9/2011 | Sanborn et al. | |
| D649,157 S | 11/2011 | Skidmore et al. | |
| 8,113,062 B2 | 2/2012 | Graboi et al. | |
| 8,181,648 B2 | 5/2012 | Perine et al. | |
| 8,210,173 B2 | 7/2012 | Vandine | |
| 8,210,174 B2 | 7/2012 | Farbarik | |
| 8,240,684 B2 | 8/2012 | Ross et al. | |
| 8,267,085 B2 | 9/2012 | Jafari et al. | |
| 8,272,379 B2 | 9/2012 | Jafari et al. | |
| 8,272,380 B2 | 9/2012 | Jafari et al. | |
| 8,302,600 B2 | 11/2012 | Andrieux et al. | |
| 8,302,602 B2 | 11/2012 | Andrieux et al. | |
| 2005/0039748 A1 | 2/2005 | Andrieux | |
| 2005/0139212 A1 | 6/2005 | Bourdon | |
| 2007/0017515 A1 | 1/2007 | Wallace et al. | |
| 2007/0077200 A1 | 4/2007 | Baker | |
| 2007/0227537 A1 | 10/2007 | Bemister et al. | |
| 2007/0284361 A1 | 12/2007 | Nadjafizadeh et al. | |
| 2008/0053441 A1 | 3/2008 | Gottlib et al. | |
| 2008/0066752 A1 | 3/2008 | Baker et al. | |
| 2008/0072896 A1 | 3/2008 | Setzer et al. | |
| 2008/0072902 A1 | 3/2008 | Setzer et al. | |
| 2008/0078390 A1 | 4/2008 | Milne et al. | |
| 2008/0083644 A1 | 4/2008 | Janbakhsh et al. | |
| 2008/0092894 A1 | 4/2008 | Nicolazzi et al. | |

(56) References Cited

U.S. PATENT DOCUMENTS

| | | | |
|---|---|---|---|
| 2008/0097234 A1 | 4/2008 | Nicolazzi et al. | |
| 2008/0249386 A1* | 10/2008 | Besterman et al. | 600/365 |
| 2009/0028057 A1 | 1/2009 | Okada et al. | |
| 2009/0131762 A1* | 5/2009 | Pelzek et al. | 600/301 |
| 2009/0165795 A1 | 7/2009 | Nadjafizadeh et al. | |
| 2009/0171176 A1 | 7/2009 | Andersohn | |
| 2009/0205661 A1 | 8/2009 | Stephenson et al. | |
| 2009/0205663 A1 | 8/2009 | Vandine et al. | |
| 2009/0241952 A1 | 10/2009 | Nicolazzi et al. | |
| 2009/0241953 A1 | 10/2009 | Vandine et al. | |
| 2009/0241956 A1 | 10/2009 | Baker, Jr. et al. | |
| 2009/0241957 A1 | 10/2009 | Baker, Jr. | |
| 2009/0241958 A1 | 10/2009 | Baker, Jr. | |
| 2009/0241962 A1 | 10/2009 | Jafari et al. | |
| 2009/0247891 A1 | 10/2009 | Wood | |
| 2009/0301486 A1 | 12/2009 | Masic | |
| 2009/0301487 A1 | 12/2009 | Masic | |
| 2009/0301490 A1 | 12/2009 | Masic | |
| 2009/0301491 A1 | 12/2009 | Masic et al. | |
| 2010/0011307 A1 | 1/2010 | Desfossez et al. | |
| 2010/0024820 A1 | 2/2010 | Bourdon | |
| 2010/0051026 A1 | 3/2010 | Graboi | |
| 2010/0051029 A1 | 3/2010 | Jafari et al. | |
| 2010/0069761 A1 | 3/2010 | Karst et al. | |
| 2010/0071689 A1 | 3/2010 | Thiessen | |
| 2010/0071692 A1 | 3/2010 | Porges | |
| 2010/0071695 A1 | 3/2010 | Thiessen | |
| 2010/0071696 A1 | 3/2010 | Jafari | |
| 2010/0071697 A1 | 3/2010 | Jafari et al. | |
| 2010/0078017 A1 | 4/2010 | Andrieux et al. | |
| 2010/0078026 A1 | 4/2010 | Andrieux et al. | |
| 2010/0081119 A1 | 4/2010 | Jafari et al. | |
| 2010/0081955 A1 | 4/2010 | Wood, Jr. et al. | |
| 2010/0139660 A1 | 6/2010 | Adahan | |
| 2010/0147303 A1 | 6/2010 | Jafari et al. | |
| 2010/0218765 A1 | 9/2010 | Jafari et al. | |
| 2010/0218766 A1 | 9/2010 | Milne | |
| 2010/0218767 A1 | 9/2010 | Jafari et al. | |
| 2010/0236555 A1 | 9/2010 | Jafari et al. | |
| 2010/0242961 A1 | 9/2010 | Mougel et al. | |
| 2010/0288283 A1 | 11/2010 | Campbell et al. | |
| 2010/0300446 A1 | 12/2010 | Nicolazzi et al. | |
| 2011/0011400 A1 | 1/2011 | Gentner et al. | |
| 2011/0023879 A1 | 2/2011 | Vandine et al. | |
| 2011/0041849 A1 | 2/2011 | Chen et al. | |
| 2011/0126832 A1 | 6/2011 | Winter et al. | |
| 2011/0126834 A1 | 6/2011 | Winter et al. | |
| 2011/0126835 A1 | 6/2011 | Winter et al. | |
| 2011/0126836 A1 | 6/2011 | Winter et al. | |
| 2011/0126837 A1 | 6/2011 | Winter et al. | |
| 2011/0138308 A1 | 6/2011 | Palmer et al. | |
| 2011/0138309 A1 | 6/2011 | Skidmore et al. | |
| 2011/0138311 A1 | 6/2011 | Palmer | |
| 2011/0138323 A1 | 6/2011 | Skidmore et al. | |
| 2011/0146681 A1 | 6/2011 | Jafari et al. | |
| 2011/0146683 A1 | 6/2011 | Jafari et al. | |
| 2011/0175728 A1 | 7/2011 | Baker, Jr. | |
| 2011/0208539 A1* | 8/2011 | Lynn | 705/2 |
| 2011/0209702 A1 | 9/2011 | Vuong et al. | |
| 2011/0209707 A1 | 9/2011 | Terhark | |
| 2011/0213215 A1 | 9/2011 | Doyle et al. | |
| 2011/0259330 A1 | 10/2011 | Jafari et al. | |

OTHER PUBLICATIONS

PCT International Search Report and Written Opinion mailed May 30, 2011; International Application No. PCT/US2011/025364; 9 pages.

7200 Series Ventilator, Options, and Accessories: Operator's Manual. Nellcor Puritan Bennett, Part No. 22300 A, Sep. 1990.

7200 Ventilatory System: Addendum/Errata. Nellcor Puritan Bennett, Part No. 4-023576-00, Rev. A, Apr. 1988.

800 Operators and Technical Reference Manual. Series Ventilator System, Nellcor Puritan Bennett, Part No. 4-070088-00, Rev. L, Aug. 2010.

840 Operator's and Technical Reference Manual. Ventilator System, Nellcor Puritan Bennett, Part No. 4-075609-00, Rev. G, Oct. 2006.

Wang, Fei-Yue & Liu, Derong (eds.), *Networked Control Systems, Theory and Applications*, Springer, London, 2008, Chapter 4: "Analysis and Design of Networked Predictive Control Systems".

* cited by examiner

EVENT-BASED DELAY DETECTION AND CONTROL OF NETWORKED SYSTEMS IN MEDICAL VENTILATION

INTRODUCTION

A ventilator is a device that mechanically helps patients breathe by replacing some or all of the muscular effort required to inflate and deflate the lungs. In recent years, there has been an accelerated trend towards an integrated clinical environment. That is, medical devices are becoming increasingly integrated with communication, computing, and control technologies. Technical advances have enabled performance enhancement and placement flexibility for sensing mechanisms that may provide monitoring capabilities, including data acquisition and transmission.

Indeed, medical ventilators may greatly benefit from a distributed network of sensing and monitoring subsystems. These subsystems may be optimally placed throughout the ventilatory system for measuring and communicating patient signals as well as for collecting diagnostic and/or physiological data. However, communication delays between distributed subsystems and a central processing platform within the medical ventilator must be adequately accounted for.

EVENT-BASED DELAY DETECTION AND CONTROL OF NETWORKED SYSTEMS IN MEDICAL VENTILATION

This disclosure describes systems and methods for detecting and quantifying transmission delays associated with distributed sensing and monitoring functions of a ventilatory system. Specifically, the present methods and systems described herein define an event-based delay detection algorithm for determining transmission delays between distributed signal measurement and processing subsystems and a central platform that receives data from these subsystems. It is important to evaluate and quantify transmission delays because dyssynchrony in data communication may result in the misalignment of visualization and monitoring systems or instability in closed-loop control systems. Generally, embodiments described herein seek to quantify transmission delays by selecting a ventilator-based defining event as a temporal baseline and calculating the delay between the inception of the defining event and the receipt of data regarding the defining event from one or more distributed sensing devices.

Embodiments of the present disclosure may include a method for determining a transmission delay associated with a distributed sensor in a ventilatory system. The method may comprise initiating a defining event and receiving a plurality of data samples after inception of the defining event from an internal sensor and from a distributed sensor. The plurality of data samples may be indexed in order of successive cycles based on data sample arrival times from the internal sensor and from the distributed sensor. The method may further calculate a first number of cycles received from the internal sensor after inception of the defining event until a first data sample breaches a threshold and calculate a second number of cycles received from the distributed sensor after inception of the defining event until a first data sample breaches the threshold. The transmission delay associated with the distributed sensor may be calculated by subtracting the first number of cycles from the second number of cycles. Data received from the internal sensor and the distributed sensor may then be synchronized based on the calculated transmission delay associated with the distributed sensor and displayed.

Further embodiments may include a ventilatory system for determining a transmission delay associated with a distributed sensor in a ventilatory system. The ventilatory system may be configured to initiate a defining event and receive a plurality of data samples after inception of the defining event from an internal sensor and from a distributed sensor. The plurality of data samples may be indexed in order of successive cycles of data sample arrival times from the internal sensor and from the distributed sensor. The ventilatory system my calculate a first number of cycles received from the internal sensor after inception of the defining event until a first data sample breaches a threshold and a second number of cycles received from the distributed sensor after inception of the defining event until a first data sample breaches the threshold. Thereafter, the transmission delay associated with the distributed sensor may be calculated by subtracting the first number of cycles from the second number of cycles. Data received from the internal sensor and the distributed sensor may be synchronized based on the calculated transmission delay associated with the distributed sensor.

Still other embodiments may include other methods for determining a transmission delay associated with a distributed sensor in a ventilatory system. The other methods may comprise initiating a defining event and receiving a plurality of data samples after inception of the defining event from an internal sensor and from a distributed sensor. The plurality of data samples may be indexed in order of successive cycles based on data sample arrival times from the internal sensor and from the distributed sensor. The other methods may calculate a first number of cycles received from the internal sensor after inception of the defining event until a first data sample breaches a threshold and a second number of cycles received from the distributed sensor after inception of the defining event until a first data sample breaches the threshold. The transmission delay associated with the distributed sensor may then be calculated by subtracting the first number of cycles from the second number of cycles. Data received from the internal sensor and the distributed sensor may be synchronized based on the calculated transmission delay associated with the distributed sensor. Synchronized data may then be analyzed for making a recommendation regarding at least one of: a patient condition and a patient treatment.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment having transmission delays associated with monitoring data.

This disclosure describes systems and methods for quantifying transmission delays between inception of a ventilator-based defining event that serves as a temporal baseline and receipt of data regarding the same defining event from one or more distributed sensing devices. Specifically, for purposes of this disclosure, a transmission delay may be defined as the interval between the time of occurrence of a measurable change associated with a defining event sensed by a distributed sensor and the time the change in measurement is received at a central platform. As transmission delays are calculated based on an actual time of inception for the ventilator-based defining event, time-stamping data is not necessary to the present methods.

Figure 1:
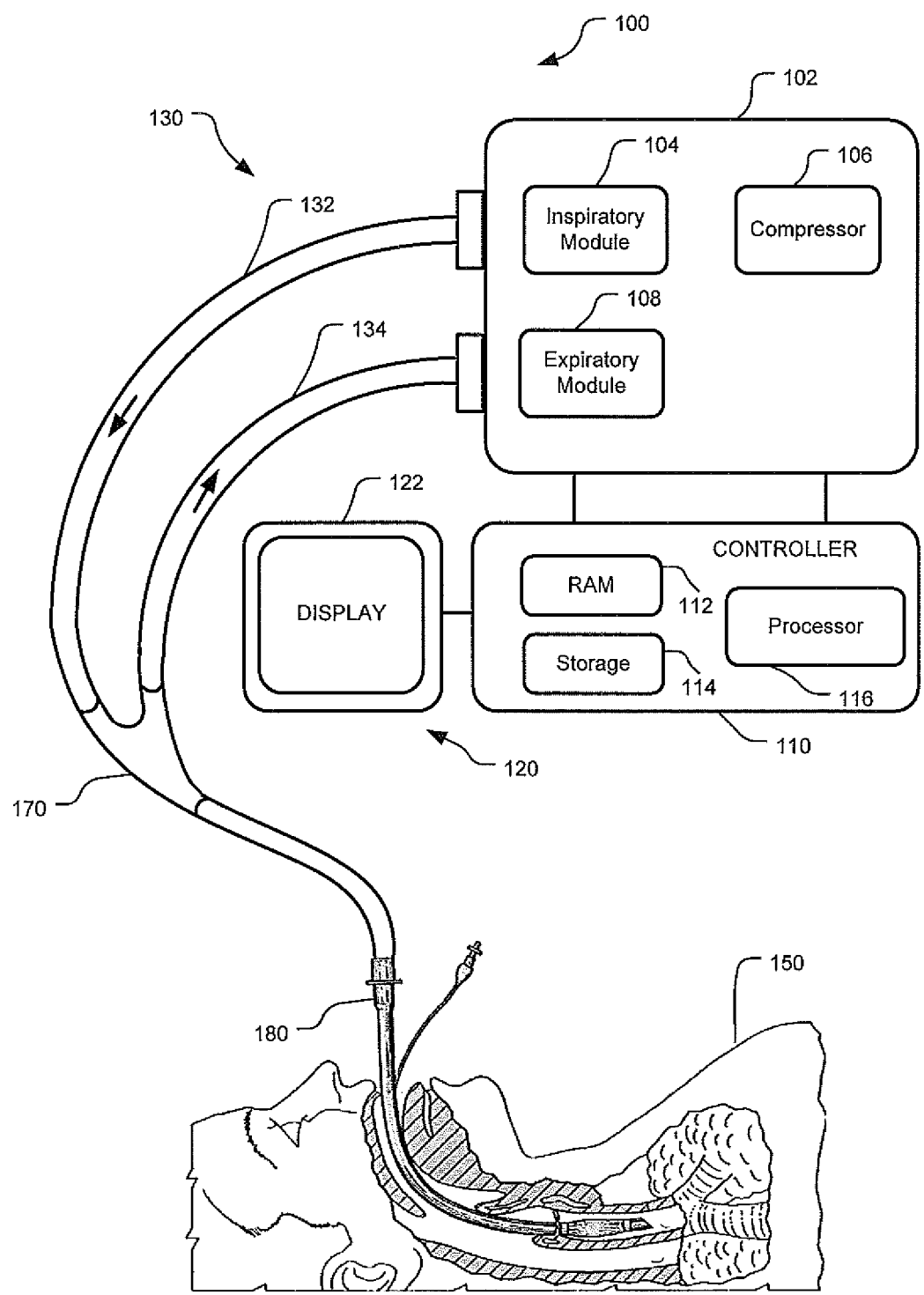
FIG. 1 is a diagram illustrating an embodiment of an exemplary ventilator connected to a human patient.

FIG. 1 illustrates an embodiment of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive (e.g., endotracheal tube, as shown) or a non-invasive (e.g., nasal mask) patient interface.

Ventilation tubing system 130 may be a two-limb (shown) or a one-limb circuit for carrying gases to and from the patient 150. In a two-limb embodiment, a fitting, typically referred to as a "wye-fitting" 170, may be provided to couple a patient interface 180 (as shown, patient interface 180 is an endotracheal tube) to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or another source(s) of pressurized gases (e.g., air, oxygen, and/or helium) is coupled with inspiratory module 104 to provide a gas source for ventilatory support via inspiratory limb 132.

The pneumatic system 102 may include a variety of other components, including sources for pressurized air and/or oxygen, mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display to serve both as an input and output device.

The memory 112 is non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. Computer-readable storage media includes non-transitory, volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 110 may monitor pneumatic system 102 in order to ensure proper functioning of the ventilator. The specific monitoring may be based on inputs received from pneumatic system 102, one or more sensors, operator interface 120, and/or other components of the ventilator. As discussed further herein, sensors may be located in optimal locations throughout the ventilatory system. For example, one or more sensors may be associated with wye-fitting 170 and/or patient interface 180. As described further herein, a sensor associated with wye-fitting 170 may be referred to as a "proximal flow sensor" and may detect changes in pressure and flow within ventilation tubing system 130.

Communication between components of the ventilatory system may be conducted over a distributed network, as described further herein, via wired or wireless means. For example, data transmission from a sensor via wired means may use serial transmission over RxD, TxD, and GND lines of a regular RS-232 interface, or via an optional USB interface. Further, the present methods may be configured as a presentation layer built over the TCP/IP protocol. TCP/IP stands for "Transmission Control Protocol/Internet Protocol" and provides a basic communication language for many local networks (such as intra- or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Figure 2:
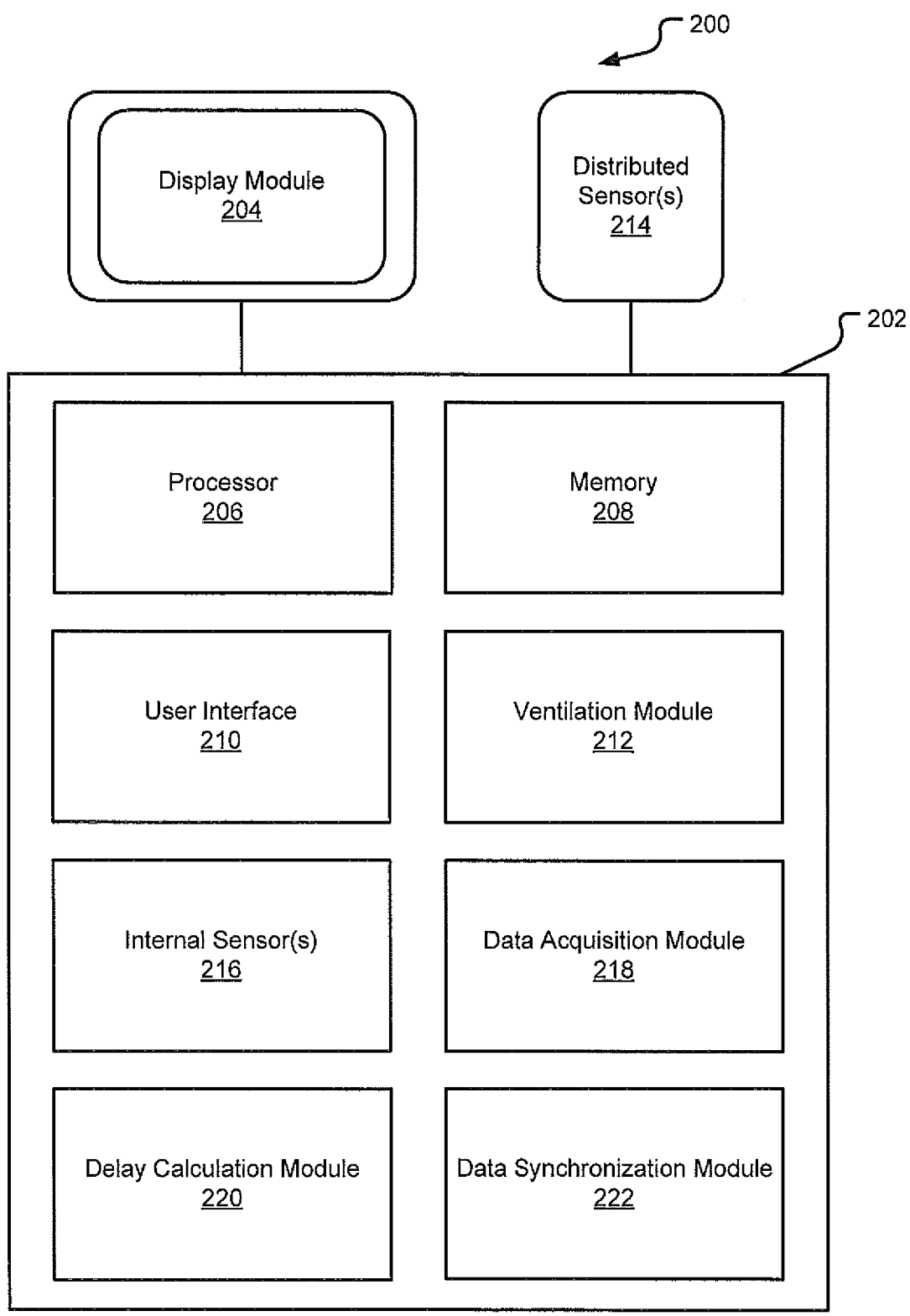
FIG. 2 is a block-diagram illustrating an embodiment of a ventilatory system for monitoring a ventilator-based defining event and quantifying delays associated with transmitting monitored data from distributed sensors.

FIG. 2 is a block-diagram illustrating an embodiment of a ventilatory system for monitoring a ventilator-based defining event and quantifying delays associated with transmitting monitored data from one or more sensors.

Ventilatory system 200 includes ventilator 202 with its various modules and components. That is, ventilator 202 may further include, inter alia, memory 208, one or more processors 206, user interface 210, and ventilation module 212. Memory 208 is defined as described above for memory 112. Similarly, the one or more processors 206 are defined as described above for the one or more processors 116. Processors 206 may further be configured with a clock whereby elapsed time may be monitored by the system 200.

Ventilation module 212 oversees ventilation as delivered to a patient according to the ventilatory settings prescribed for the patient. By way of general overview, the basic elements impacting ventilation may be described by the following ventilatory equation (also known as the Equation of Motion, applicable during both inspiration and expiration):

$$P_m + P_v = V/C + R*F$$

Here, $P_m$ is a measure of muscular effort that is equivalent to the pressure generated by the muscles of a patient. If the patient's muscles are inactive, the $P_m$ is equivalent to 0 cm $H_2O$. During inspiration, $P_v$ represents the positive pressure delivered by a ventilator (generally in cm $H_2O$). This ventilatory pressure, $P_v$, represents ventilatory circuit pressure, i.e., the pressure gradient between the airway opening and the ambient pressure to which the patient's body surface is exposed. For example, for positive pressure ventilation, pressure at the upper airway is positive relative to the pressure at the body's surface (i.e., relative to the ambient atmospheric pressure, which is set to 0 cm $H_2O$). This pressure gradient is what allows air to flow into the airway and ultimately into the lungs of a patient during inspiration (or, inhalation). V represents the volume delivered, C refers to the respiratory compliance, R represents the respiratory resistance, and F represents the gas flow during inspiration (generally in liters per min (lpm)). As such, where other variables are known, upon detecting changes in $P_v$, flow may be derived by the ventilator.

With reference to the ventilatory equation above, ventilation module 212 may deliver air pressure during inspiration into the ventilatory circuit, and thereby into a patient's lungs, by any suitable method, either currently known or disclosed in the future. Specifically, ventilation module 212 may be in communication with inspiratory module 104 coupled to compressor 106, or other source(s) of pressurized gases (e.g., air, oxygen, and/or helium), to provide a gas source for delivering air pressure via inspiratory limb 132. As noted above, delivery of air pressure to the upper airway will create a pressure gradient that enables gases to flow into a patient's lungs, i.e., positive flow. The pressure from which a ventilator initiates inspiration is termed the "baseline" pressure. This pressure may be atmospheric pressure (0 cm $H_2O$), also called zero end-expiratory pressure (ZEEP). Alternately, the baseline pressure may be positive, termed positive end-expiratory pressure (PEEP).

During inspiration, gas flow is delivered to a patient until a desired pressure or flow target is reached based on a reference trajectory and/or a set time, and subsequently the transition to expiration may be initiated. By way of general overview, a ventilator initiates expiration based on an inspiratory time setting or other cycling criteria set by the clinician or derived from ventilator settings. Upon initiating an expiratory phase, the ventilator allows the patient to exhale by opening an expiratory valve associated with, for example, expiratory module 108. As such, expiration is passive, and the direction of airflow, as described above, is governed by the pressure gradient between the patient's lungs and the ambient surface pressure. Thus, the higher the pressure difference across the expiratory valve, the higher the resultant expiratory flow in the circuit, i.e., negative flow. As the increment of flow change leaving the patient's lungs through the expiratory module is dependent on the resistance of the pneumatic path (expiratory valve, circuit, etc.), expiratory flow may be governed at least in part by the magnitude of the size of the opening of the expiratory valve. Note that at the point of transition between inhalation and exhalation, the direction of airflow abruptly changes from a positive flow (into the lungs) to a negative flow (out of the lungs).

The ventilatory system 200 may also include a display module 204 communicatively coupled to ventilator 202. Display module 204 provides various input screens, for receiving clinician input, and various display screens, for presenting useful information to the clinician. The display module 204 is configured to communicate with user interface 210 and may include a graphical user interface (GUI). The GUI may further provide various windows and elements to the clinician for input and interface command operations. Alternatively, user interface 210 may provide other suitable means of communication with the ventilator 202, for instance by a keyboard or other suitable interactive device.

The ventilatory system 200 may also include one or more distributed sensors 214 communicatively coupled to ventilator 202. Distributed sensors 214 may detect changes in measurable parameters indicative of a patient's condition and/or ventilatory treatment. Distributed sensors 214 may further include semi-autonomous sensing units with independent and/or unidentified electronic conditioning and signal processing hardware and firmware. Distributed sensors 214 may be placed in any suitable location, e.g., within the ventilatory circuitry or other devices communicatively coupled to the ventilator. For example, sensors may be affixed to the ventilatory tubing or may be imbedded in the tubing itself. Additionally or alternatively, sensors may be affixed or imbedded in or near wye-fitting 170 and/or patient interface 180, as described above. Distributed sensors 214 may further include pressure transducers and may be attached at various locations along the ventilatory circuit to detect changes in circuit pressure and/or flow. Alternatively, sensors may utilize optical or ultrasound techniques for measuring changes in circuit pressure and/or airflow. A patient's blood parameters or concentrations of expired gases may also be monitored by sensors to detect physiological changes that may be used as indicators to study physiological effects of ventilator-based events, wherein the results of such studies may be used for diagnostic or therapeutic purposes. Indeed, any distributed sensory device useful for monitoring changes in measurable parameters during ventilatory treatment may be employed in accordance with embodiments described herein.

For example, distributed sensors 214 may include a proximal flow sensor, as described above. The proximal flow sensor may be placed close to the patient wye-fitting and may acquire raw data for further processing. That is, the proximal flow sensor may acquire raw data regarding differential pressure and flow readings for further processing and derivation by the ventilator. More specifically, distributed sensors 214 may monitor airway pressure data during a suitable ventilator-based defining event. A suitable ventilator-based defining event may include any number of events that may be detectable throughout ventilatory system 200. For example, these events should be reliably detected by both internal sensors 216, described below, and distributed sensors 214. Additionally, these events should be chosen such that there exists a one-to-one temporal correspondence between the timeline of the initiation of the defining event, as registered by a leading sensor, and a corresponding expected change in the signal, as registered by a trailing sensor (i.e., trailing would correspond to data transfer and not event registration). So, when there is an inherent time delay between a ventilation change (e.g., delivered Oxygen mix) and a corresponding physiological change (e.g., blood oxygen concentration), such events should not be used as defining events for signal delay determination. Specifically, then, a ventilator-based defining event is a deterministic physical occurrence within the ventilator's time framework and, as such, may serve as the basis for temporal alignment of inter-related signals from various distributed sensors pertaining to the same event.

For example, a ventilator-based defining event may be initiated by the ventilator at a particular time, t=0, known to the ventilator (e.g., the ventilator initiates the transition between inspiration and expiration by opening of an expiratory valve at time zero). Indeed, inception of a ventilator-based defining event may be set to time zero regardless of why the ventilator initiated the defining event, i.e., it is irrelevant whether the ventilator initiated expiration in response to patient signals from a spontaneously-breathing patient or whether the ventilator initiated expiration based on a prescribed schedule for a passive patient. Thereafter, the time of arrival for data collected from external sensors may be compared to the inception (at time zero as detected by internal sensors) of the ventilator-based defining event. As a result, ventilator-based defining events may be used to synchronize the timing of signals received from internal and distributed network sensors.

For example, as noted above, suitable ventilator-based defining events may include inhalation/exhalation transitions (also known as "Breath Cycling"). A cycling event, e.g., the transition between inspiration and expiration, may be selected as a defining event because there is an abrupt and reliable drop in airway pressure concomitant with a directional change in lung flow during the transition between inspiration and expiration. Additional suitable ventilator-based defining events may also be selected, including the transition between expiration and inspiration, a recruitment maneuver event, etc. Specifically, for a selected defining event comprising the transition between inspiration and expiration, an internal sensor and a proximal flow sensor may collect and save airway pressure data for a definite number of samples, e.g., 20 samples (each corresponding to a 5 millisecond sampling period), the total acquisition frame corresponding to a window of 100 milliseconds (ms) from the inception of the defining event. The proximal flow sensor's final outputs may be communicated to the ventilator via serial transmission over RxD, TxD, and GND lines of a regular RS-232 interface, or via other means such as an optional USB interface. Arrival times for data from both the internal sensor and the proximal flow sensor at a central platform of the ventilator may then be compared to the inception of the defining event (designated as time zero by the ventilator).

As noted above, distributed sensors 214 may communicate with various components of ventilator 202, e.g., ventilation module 212, internal sensors 216, data acquisition module 218, delay calculation module 220, and any other suitable components and/or modules. For purposes of the present disclosure, the disclosed and undisclosed processing, memory, and other modules and components of ventilator 202 may collectively represent the central platform of the ventilator, as described herein. As described above, distributed sensors 214 may transmit monitored data over a network with ventilator 202 via wired or wireless means. Further, the transmission of monitored data may be delayed for various reasons before reaching destination components of the ventilator 202. Transmission delays may occur for a variety of reasons, including delays attributed to sensing mechanisms within one or more distributed sensors 214, delays related to signal processing operations, data acquisition and conversion delays, and network delays, inter alga. As noted previously, transmission delays may lead to dyssynchrony and misalignment in visualization and monitoring systems or instability in closed-loop control systems and should be adequately quantified and accounted for.

Ventilator 202 may further include one or more internal sensors 216. Similar to distributed sensors 214, internal sensors 216 may employ any suitable sensory or derivative technique for monitoring one or more parameters associated with the ventilation of a patient. However, the one or more internal sensors 216 may be placed in any suitable internal location, such as, within the ventilatory circuitry or within components or modules of ventilator 202. For example, sensors may be coupled to the inspiratory and/or expiratory modules for detecting changes in, for example, circuit pressure and flow. Specifically, internal sensors may include pressure transducers for measuring changes in pressure and/or airflow. Additionally or alternatively, internal sensors may utilize optical or ultrasound techniques for measuring changes in ventilatory parameters. For example, a patient's blood or expired gases may be monitored by internal sensors to detect physiological changes indicative of a defining event of interest. Indeed, internal sensors may employ any suitable mechanism for monitoring parameters of interest in accordance with embodiments described herein.

As described above with reference to distributed sensors 214, for a selected defining event comprising the transition between inspiration and expiration, internal sensors 216 may independently collect and save airway pressure data for a definite number of samples, e.g., 20 samples corresponding to a window of 100 milliseconds (ms) from the inception of the defining event. According to a described embodiment, data from internal sensors 216 correlates with the internal timeline of the ventilator, i.e., the internal sensors are leading sensors and provide the temporal baseline for a selected defining event, as described herein. In alternative embodiments, a defining event may be selected such that one or more distributed sensors may detect data associated with the defining event prior to the internal sensors. In that case, a first distributed sensor to detect data associated with the defining event (i.e., the leading sensor) may provide the temporal baseline for the defining event and the data from trailing sensors (i.e., other distributed sensors and the internal sensors) may be synchronized with the first distributed sensor.

Ventilator 202 may further include a data acquisition module 218. As noted above, internal and external sensors may independently collect and save airway pressure or flow data. These sensors may further transmit collected data to the data acquisition module 218 for indexing. Specifically, data acquisition module 218 may save data received from sensors (both internal and distributed) in buffers and may index the data according to a sample acquisition sequence, or successive acquisition cycles, based on data arrival times. As noted above, according to an embodiment, internal sensors may be leading sensors and may correlate with the ventilator's internal timing framework. According to this embodiment, distributed sensors may be trailing sensors and data samples received from the distributed sensors may be delayed by a particular number of acquisition cycles behind the internal sensors. A total data collection interval may be determined based on an expected maximum delay plus a safety margin.

Ventilator 202 may further include a delay calculation module 220. Delay calculation module 220 may retrieve data from data acquisition module 218, or other suitable module, for determining a delay coefficient associated with each of the one or more distributed sensors 214. For example, utilizing pressure data obtained from the one or more internal sensors 216, delay calculation module 220 may compute the number of acquisition cycles (e.g., $N_{vent}$) from the inception of the selected defining event (pressure drop as registered by an internal sensor) until a first cycle indicating a pressure drop breaching a threshold magnitude (e.g., a pressure drop of 0.5 cm $H_2O$ or more). Indeed, a variety of metrics may be devised for this comparison based on design requirements and signal characteristics. In the described embodiment, airway pressure values are utilized (and may be processed to reduce signal noise), but other metrics are possible. For instance, a ratiometric indicator of change calculated as the ratio of instantaneous signal magnitude divided by the sum of the initial signal magnitude (i.e., the signal magnitude at the first expiration cycle or FEP) and a fixed constant (to prevent division by zero in the case of FEP=0). Alternative methods such as waveform-matching routines like algorithms based on cross-correlation techniques may be used as appropriate for design requirements and resource economy.

Delay calculation module 220, utilizing pressure data obtained from the one or more distributed sensors 214, may conduct the same comparison. For example, based on data received from a distributed sensor, delay calculation module 220 may also compute the number of acquisition cycles (e.g., $N_{dist}$) from the inception of the selected defining event (i.e., time zero as determined by the ventilator's internal time framework, discussed above) until a first cycle is received indicating a breach of the same criteria (e.g., a pressure drop of 0.5 cm $H_2O$ or more) as registered and transmitted by a distributed, or trailing, sensor.

Thereafter, delay calculation module 220 may calculate the delay associated with one or more distributed sensors 214 for the selected defining event. Specifically, the sensor delay for the distributed sensor as described above may be represented as follows:

$$SensorDelay_{dist} = N_{dist} - N_{vent}$$

In order to account for statistical variations, data may be collected for a number of consecutive breaths (e.g., consecutive defining events corresponding to transitions between inspiration and expiration). For example, data may be received and saved from both the internal sensors 216 and the distributed sensors 214 for five consecutive defining events. A delay coefficient associated with each of the distributed sensors 214 may be calculated based on the data collected from the five consecutive defining events. The delay coefficient may then be used for ventilator synchronization purposes related to each of the distributed sensors 214. For example, the delay coefficient for the distributed sensor discussed above may be represented as:

$$SensorDelayCoef_{dist} = median(SensorDelay_{dist(1)} \ldots SensorDelay_{dist(5)})$$

Here, median ( ) refers to a function for calculating a statistical median (i.e., the middle value of $SensorDelay_{dist}$ collected for the five consecutive defining events). According to other embodiments, calculating the mean or average of $SensorDelay_{dist(1)} \ldots SensorDelay_{dist(5)}$) may be more appropriate for purposes of determining the $SensorDelayCoef_{dist}$. Indeed, any calculation accounting for statistical variations in the data may be employed within the spirit of the present disclosure.

The ventilator 202 may further include a data synchronization module 222. Data synchronization module 222 may utilize delay coefficients for each of a plurality of distributed sensors to synchronize data streams transmitted from each of the plurality of distributed sensors. Specifically, the data stream transmitted from each distributed sensor may be temporally aligned with data streams from other sensors based on each distributed sensor's delay coefficient. As such, data streams arriving from the plurality of distributed sensors may be synchronized for display to a clinician, e.g., via waveforms, graphs, etc., according to a common temporal axis. In addition, synchronized data may be analyzed by the ventilator for presenting recommendations to a clinician regarding a patient's condition and/or treatment or for initiating closed-loop control operations.

Figure 3:
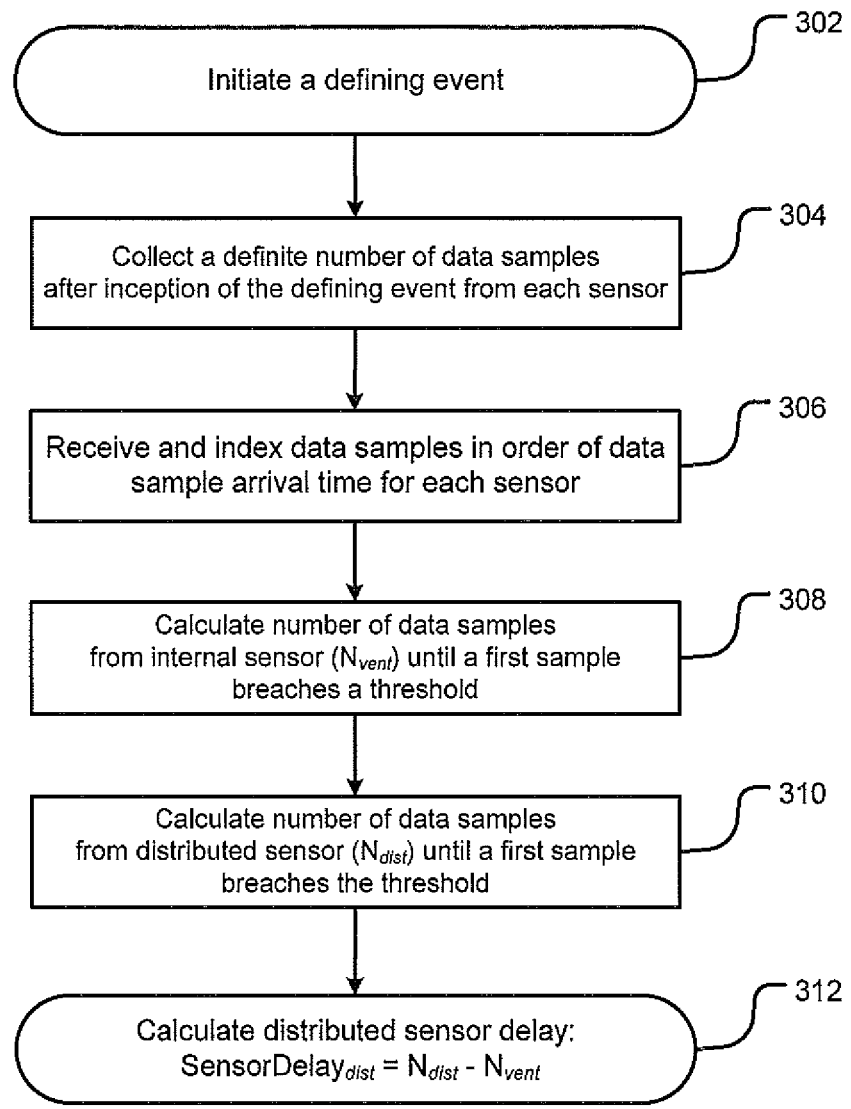
FIG. 3 is a flow chart illustrating an embodiment of a method for calculating a distributed sensor transmission delay in a ventilatory system.

FIG. 3 is a flow chart illustrating an embodiment of a method for calculating a distributed sensor transmission delay in a ventilatory system.

At initiate defining event operation 302, the ventilator may initiate a ventilator-based defining event at time zero. As previously noted, any number of defining events may be appropriately utilized for determining transmission delays associated with distributed sensors. However, for purposes of the present disclosure, the transition between inspiration and expiration (i.e., a cycling event) will be illustrated and discussed as the defining event. As such, for a passive patient, the ventilator may detect that the cycling criteria has been met and that transition into expiration ought to be initiated, for example. Alternatively, for a spontaneously-breathing patient, the ventilator may detect a change in patient effort, signaling that expiration ought to be initiated. In either case, the ventilator may initiate the transition into expiration by opening the expiratory valve, as described above. The inception of the defining event, then, corresponds to the ventilator beginning to open the expiratory valve at time zero and detection by an internal sensor of a measurable change in a signal such as pressure.

At collect data samples operation 304, internal and distributed sensors may collect data samples associated with the defining event. For example, each sensor may collect 20 pressure data samples over a 100 ms period from inception of the defining event. As described above, any definite number of data samples over a specific time period following inception of the defining event may be appropriate and well within the spirit of the present disclosure.

At index operation 306, the ventilator's data acquisition module may collect data from multiple internal as well as distributed sensors at definite sampling rates (with known sampling periods separating each consecutive reading) and may receive and index collected data samples from each sensor. That is, the ventilator may save data samples from each sensor in buffers and may index, or order, the data samples according to their arrival times at the ventilator. Although multiple internal and distributed sensors are possible within the scope of the present disclosure, an embodiment involving a single internal sensor, a single distributed sensor, and a data acquisition module with a fixed sampling period (e.g., 5 ms) that produces a single measurement sample per acquisition cycle will be discussed herein. As noted above, according to a described embodiment, the internal sensor may be a leading sensor (used for time reference) and data received from the internal sensor may, thus, establish the timeline for the defining event. Alternatively, the distributed sensor may be a trailing sensor and arrival times for data samples from the distributed sensor may be delayed, as described above, by a number of acquisition periods (of known duration) behind the data received from the internal sensor. The duration of each acquisition cycle (period between two consecutive readings) is one of the characteristics of the data acquisition module.

At calculate $N_{vent}$ operation 308, the ventilator may count a number of samples of data (e.g., $N_{vent}$) received from the internal sensor after inception of the defining event until a first cycle in which a data sample breaches a threshold value as measured by the reference (leading) sensor. For example, the threshold value may be a pressure of 0.5 cm H$_2$O and the ventilator may calculate the number of cycles from the inception of the defining event to a first cycle indicating a drop in circuit pressure of 0.5 cm H$_2$O or more. As noted above, metrics using data samples other than pressure values are possible and well within the scope of the present disclosure.

At calculate N$_{dist}$ operation 310, the ventilator may count the number of samples of data (e.g., N$_{dist}$) received from the distributed sensor after inception of the defining event until the first cycle having a data sample that breaches the same threshold value. Referring to the example above, the ventilator may calculate the number of samples received from the distributed sensor after the inception of the defining event until a first cycle indicating a drop in circuit pressure of 0.5 cm H$_2$O or more as measured by the distributed sensor. In some embodiments, the distributed sensor may be a proximal flow sensor, as described above.

At calculate SensorDelay$_{dist}$ operation 312, the ventilator may determine a delay associated with the distributed sensor. That is, the ventilator may determine a number of cycles that data from the distributed sensor is delayed behind data of the internal sensor for the defining event. For example, the ventilator may calculate the SensorDelay$_{dist}$ as follows:

$$\text{SensorDelay}_{dist} = N_{dist} - N_{vent}$$

In some embodiments, the ventilator may further calculate the delay for the distributed sensor in terms of a time estimate. For example, according to the described embodiment, if 20 data samples were collected over 100 ms, a data sample was collected every 5 ms from each sensor. Thus, a time estimate of the delay may be represented as the product of the number of delayed cycles by the 5 ms sampling period, i.e.:

$$5\text{ ms/cycle} * \text{SensorDelay}_{dist}(\text{cycles}) = \text{SensorDelay}_{dist}(\text{ms})$$

The above time delay is an estimate because it assumes that data samples will arrive at the ventilator a fixed rate regardless of any sampling period (or frequency) jitter. Furthermore, in data acquisition modules, data are updated at definite sampling intervals during which an acquired value remains the same until the next sampling period (sample and hold operation). Thus, a change in the signal of interest may occur at any time during a sampling period (e.g., 5 or 10 ms interval) and will be assigned to that cycle regardless of the exact time of occurrence. Therefore, only an estimated time delay is determined by the above calculation and the accuracy of the estimated values is a function of multiple factors including signal acquisition characteristics. It is understood that different sensors may be sampled at different rates and the corresponding sampling intervals may be known.

In another embodiment, a more accurate estimate of the average sampling period may be calculated by taking a total time measurement (measured by an independent clock, when available, which is different from the timing mechanism used by the data acquisition module) for a finite number of cycles, n, (i.e., time of receipt of first cycle until time of receipt of nth cycle, designated an acquisition frame) divided by n samples (e.g., 100 ms acquisition frame/20 samples=5 ms). This calculation provides an estimate of the average receipt time per cycle. Thereafter the average receipt time per cycle (average sampling period) may be multiplied by the SensorDelay$_{dist}$ to provide a time estimate of the delay as follows:

$$\text{Acquisition frame(ms)}/n(\text{cycles}) * \text{SensorDelay}_{dist}(\text{cycles}) = \text{SensorDelay}_{dist}(\text{ms})$$

Figure 4:
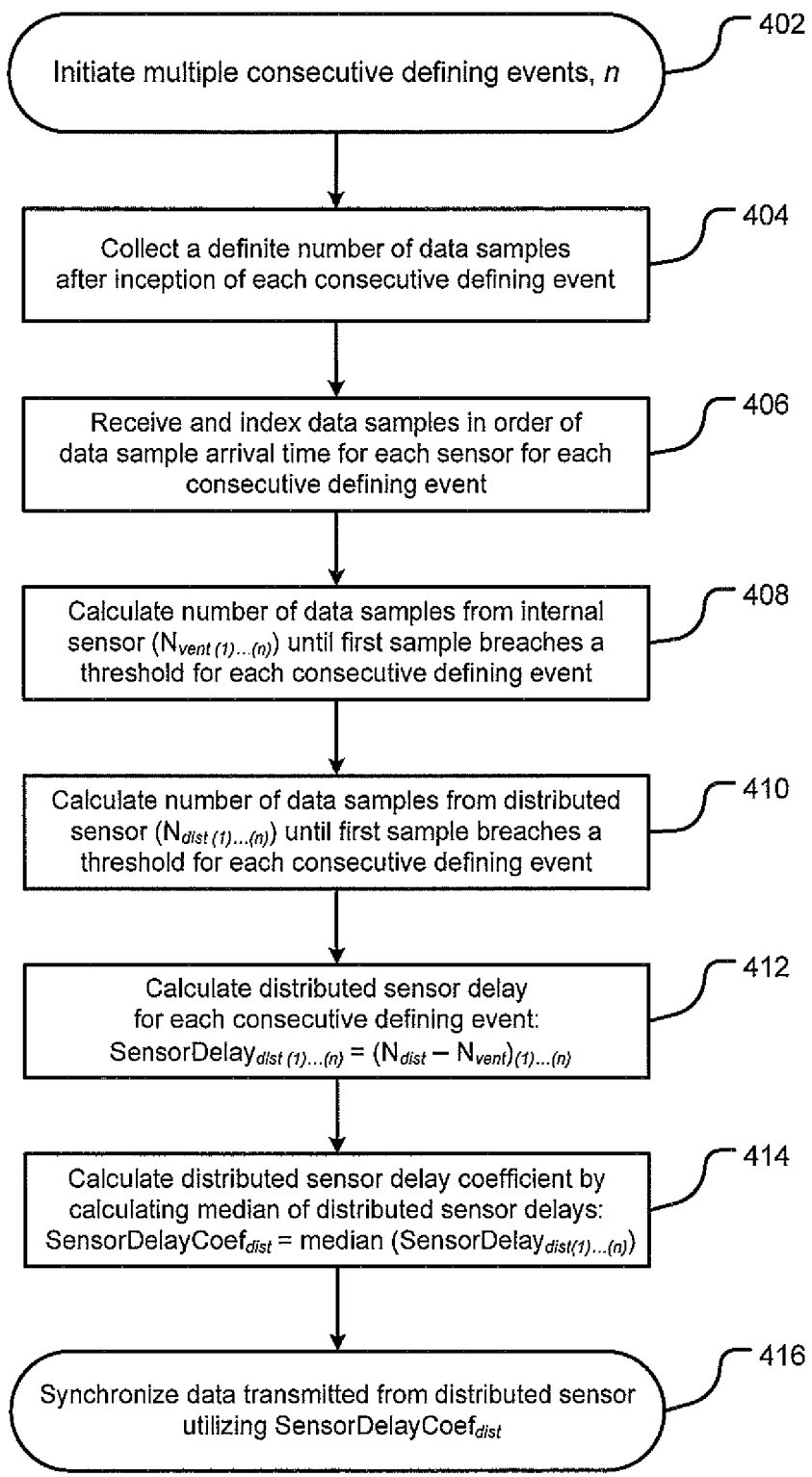
FIG. 4 is a flow chart illustrating an embodiment of a method for calculating a distributed sensor delay coefficient in a ventilatory system.

FIG. 4 is a flow chart illustrating an embodiment of a method for calculating a distributed sensor delay coefficient in a ventilatory system.

At initiate multiple defining events operation 402, the ventilator may initiate a number of consecutive defining events. For example, the ventilator may initiate multiple defining events comprising transitions between inspiration and expiration for a number of consecutive breaths, e.g., five breaths. In accordance with the discussion above, inception of each consecutive defining event may be reset to time zero by the ventilator.

At collect data samples operation 404, the internal and distributed sensor readings may be collected by the ventilator data acquisition module to collect data samples for each consecutive defining event. For example, 20 pressure data samples may be collected from each of the sensors over a 100 ms period from the inception of each consecutive defining event.

At index operation 406, the ventilator may receive and index collected data samples from each sensor for each consecutive defining event. That is, the ventilator may save data samples from each sensor for each consecutive defining event in buffers and may index the data samples according to successive acquisition cycles based on their arrival times at the ventilator. As noted above, where the internal sensor is a leading sensor, data samples received from the internal sensor may establish the temporal baseline for each consecutive defining event. Consequently, where the distributed sensor is a trailing sensor, arrival times for data samples from the distributed sensor for each consecutive defining event may be delayed, as described above.

At calculate N$_{vent(1)\ldots(n)}$ operation 408, for each consecutive defining event, the ventilator may determine a number of samples of data (e.g., N$_{vent(1)\ldots(n)}$) received from the internal sensor following inception of each consecutive defining event (e.g., 1 through n) until a first cycle having a data sample that indicates a breach of a threshold value. For example, the ventilator may calculate the number of data samples from the inception of each consecutive defining event until a first cycle indicating a drop in circuit pressure of 0.5 cm H$_2$O or more.

At calculate N$_{dist(1)\ldots(n)}$ operation 410, for each consecutive defining event, the ventilator may determine the number of samples of data (e.g., N$_{dist(1)\ldots(n)}$) received from the distributed sensor following inception of each consecutive defining event (e.g., 1 through n) until a first cycle having a data sample that indicates a breach of the same threshold value as registered by the distributed sensor. Again referring to the example above, the ventilator may calculate the number of data samples received from the distributed sensor after the inception of each consecutive defining event until a first cycle having a data samples indicating a drop in circuit pressure of 0.5 cm H$_2$O or more. As above, in some embodiments, the distributed sensor may be a proximal flow sensor.

At calculate SensorDelay$_{dist(1)\ldots(n)}$ operation 412, for each consecutive defining event, the ventilator may determine a delay associated with the distributed sensor. That is, the ventilator may determine a number of cycles in which data from the distributed sensor is delayed behind data of the internal sensor for each consecutive defining event. For example, the ventilator may calculate a set of consecutive distributed sensor delays (e.g. 1 through n) as follows:

$$\text{SensorDelay}_{dist(1)\ldots(n)} = (N_{dist} - N_{vent})(1)\ldots(n)$$

At calculate distributed sensor delay coefficient operation 414, the ventilator may determine a delay coefficient for the distributed sensor. Specifically, the ventilator may calculate the median of the set of consecutive distributed sensor delays as follows:

$$SensorDelayCoef_{dist} = median(SensorDelay_{dist(1)\ldots(n)})$$

Here, median ( ) refers to a function for calculating a statistical median (i.e., the middle value of the set of consecutive distributed sensor delays, $SensorDelay_{dist(1)\ldots(n)}$). As noted above, other calculations that account for statistical variations in the $SensorDelay_{dist(1)\ldots(n)}$ values may be employed within the spirit of the present disclosure.

At synchronize data operation 416, the ventilator may use the $SensorDelayCoef_{dist}$ to align data streams transmitted from the distributed sensor with data streams transmitted from other sensors. Specifically, in some embodiments, the synchronized data may be displayed to a clinician in the form of data values, wave forms, graphs, or other suitable forms of display. In other embodiments, synchronized data may be analyzed by the ventilator in order to make recommendations to the clinician regarding a patient's condition and/or treatment, e.g., in the form of smart prompts or otherwise. For example, based on synchronized data received from internal and distributed sensors, the ventilator may determine that differential pressure readings indicate a leak or occlusion within the ventilatory circuit. As such, an appropriate alert may be presented to a clinician regarding the ventilator's assessment of the synchronized data. In still other embodiments, the synchronized data may be utilized by the ventilator for closed-loop control operations, e.g., adjusting one or more ventilatory settings in response to an evaluation of the synchronized data and protocols specifying appropriate corresponding adjustments while applying appropriate predictive methods to compensate for measurement delays. For example, appropriate settings adjustments may include, inter alia, increasing or decreasing a PEEP setting, increasing or decreasing an Inspiratory Pressure target setting, increasing or decreasing a $FiO_2$ setting, or any other suitable settings adjustment as prescribed by an appropriate protocol or specification.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method implemented by a ventilator system comprising at least one processor and at least one memory, the at least one memory storing computer-readable instructions that when executed by the at least one processor cause the ventilator system to perform a method for determining a transmission delay associated with a distributed sensor in the ventilator system, the method comprising:
   initiating, by the ventilator system, a defining event;
   receiving a first plurality of data samples for a parameter after inception of the defining event from an internal sensor;
   receiving a second plurality of data samples for the parameter after inception of the defining event from a distributed sensor;
   indexing the first plurality of data samples in order of successive cycles based on data sample arrival times from the internal sensor;
   indexing the second plurality of data samples in order of successive cycles based on data sample arrival times from the distributed sensor;
   calculating a first number of cycles received from the internal sensor after inception of the defining event until a first data sample of the first plurality of data samples breaches a threshold associated with the parameter;
   calculating a second number of cycles received from the distributed sensor after inception of the defining event until a first data sample of the second plurality of data samples breaches the threshold associated with the parameter;
   calculating, by the ventilator system, the transmission delay associated with the distributed sensor by subtracting the first number of cycles from the second number of cycles, wherein the transmission delay is represented as a number of cycles;
   synchronizing data received from the internal sensor and the distributed sensor based on the calculated transmission delay associated with the distributed sensor; and
   analyzing, by the ventilator system, the synchronized data in order to identify at least one of a leak and an occlusion in a ventilatory circuit.

2. The method of claim 1, wherein the defining event is a transition from inspiration to expiration.

3. The method of claim 1, wherein the first plurality of data samples comprises 20 data samples collected over 100 milliseconds (ms) after the inception of the defining event by the internal sensor and the second plurality of data samples comprises 20 data samples collected over 100 milliseconds (ms) after the inception of the defining event by the distributed sensor.

4. The method of claim 1, wherein the distributed sensor is a proximal flow sensor.

5. The method of claim 1, wherein the threshold is a circuit pressure change of 0.5 cm $H_2O$, and wherein the threshold is breached when a data sample indicates that circuit pressure dropped by 0.5 cm $H_2O$ or more.

6. The method of claim 1, further comprising:
   initiating a plurality of consecutive defining events comprising a transition from inspiration to expiration for each of a plurality of consecutive breaths.

7. The method of claim 6, further comprising:
   calculating a set of distributed sensor delays, wherein the set of distributed sensor delays comprises a distributed sensor delay for each of the plurality of consecutive defining events; and
   calculating a median of the set of distributed sensor delays to yield a distributed sensor delay coefficient.

8. The method of claim 7, further comprising:
   synchronizing the data received from the internal sensor and the distributed sensor based on the distributed sensor delay coefficient.

9. A method implemented by a ventilator system comprising at least one processor and at least one memory, the at least one memory storing computer-readable instructions that when executed by the at least one processor cause the ventilator system to perform a method for determining a transmission delay associated with a distributed sensor in the ventilator system, the method comprising:
- initiating, by the ventilator system, a defining event;
- receiving a first plurality of data samples for a parameter after inception of the defining event from an internal sensor;
- receiving a second plurality of data samples for the parameter after inception of the defining event from a distributed sensor;
- indexing the first plurality of data samples in order of successive cycles based on data sample arrival times from the internal sensor;
- indexing the second plurality of data samples in order of successive cycles based on data sample arrival times from the distributed sensor;
- calculating a first number of cycles received from the internal sensor after inception of the defining event until a first data sample of the first plurality of data samples breaches a threshold associated with the parameter;
- calculating a second number of cycles received from the distributed sensor after inception of the defining event until a first data sample of the second plurality of data samples breaches the threshold associated with the parameter;
- calculating the transmission delay associated with the distributed sensor by subtracting the first number of cycles from the second number of cycles, wherein the transmission delay is represented as a number of cycles;
- synchronizing data received from the internal sensor and the distributed sensor based on the calculated transmission delay associated with the distributed sensor; and
- analyzing the synchronized data for making a recommendation regarding at least one of: a patient condition and a patient treatment.

10. The method of claim 9, further comprising:
initiating a plurality of consecutive defining events comprising a transition from inspiration to expiration for each of a plurality of consecutive breaths.

11. The method of claim 10, further comprising:
calculating a set of distributed sensor delays, wherein the set of distributed sensor delays comprises a distributed sensor delay for each of the plurality of consecutive defining events; and
calculating a median of the set of distributed sensor delays to yield a distributed sensor delay coefficient.

12. The method of claim 11, further comprising:
synchronizing the data received from the internal sensor and the distributed sensor based on the distributed sensor delay coefficient.

* * * * *